US012012500B2

(12) United States Patent
Ross et al.

(10) Patent No.: US 12,012,500 B2
(45) Date of Patent: Jun. 18, 2024

(54) LOW FREE 2-MERCAPTOETHANOL ESTER AND USES THEREOF

(71) Applicant: PMC ORGANOMETALLIX, INC., Mount Laurel, NJ (US)

(72) Inventors: Kevin John Ross, Rockwood (CA); Gene Kelly Norris, West Chester, OH (US); Jeremy Dunlap, Walton, KY (US)

(73) Assignee: PMC Organometallix, Inc., Mount Laurel, NJ (US)

( * ) Notice: Subject to any disclaimer, the term of this patent is extended or adjusted under 35 U.S.C. 154(b) by 273 days.

(21) Appl. No.: 17/135,594

(22) Filed: Dec. 28, 2020

(65) Prior Publication Data

US 2021/0188768 A1   Jun. 24, 2021

Related U.S. Application Data

(63) Continuation of application No. 16/554,275, filed on Aug. 28, 2019, now abandoned.

(60) Provisional application No. 62/878,040, filed on Jul. 24, 2019, provisional application No. 62/723,943, filed on Aug. 28, 2018.

(51) Int. Cl.
| | |
|---|---|
| *C08K 5/58* | (2006.01) |
| *C07C 319/12* | (2006.01) |
| *C07C 319/28* | (2006.01) |
| *C07C 323/12* | (2006.01) |
| *C08K 5/00* | (2006.01) |
| *C08K 5/36* | (2006.01) |
| *C08K 5/37* | (2006.01) |
| *C08K 5/57* | (2006.01) |
| *C08L 27/06* | (2006.01) |

(52) U.S. Cl.
CPC .............. *C08K 5/58* (2013.01); *C07C 319/12* (2013.01); *C07C 319/28* (2013.01); *C07C 323/12* (2013.01); *C08K 5/0016* (2013.01); *C08K 5/36* (2013.01); *C08K 5/37* (2013.01); *C08K 5/57* (2013.01); *C08L 27/06* (2013.01); *C08L 2201/08* (2013.01)

(58) Field of Classification Search
CPC ... C07C 323/12; C07C 319/12; C07C 319/28; C08K 5/58; C08K 5/37; C08K 5/0016; C08K 5/36; C08K 5/57; C08L 27/06; C08L 2201/08
See application file for complete search history.

(56) References Cited

U.S. PATENT DOCUMENTS

| | | | |
|---|---|---|---|
| 3,565,931 | A | 2/1971 | Brecker |
| 4,062,881 | A | 12/1977 | Kugele |
| 4,120,845 | A | 10/1978 | Kugele |
| 4,532,286 | A | 7/1985 | Rosenberger |
| 6,846,861 | B2 | 1/2005 | Herzig et al. |
| 6,919,392 | B1 | 7/2005 | Chenard et al. |
| 2006/0069195 | A1 | 3/2006 | Barda |
| 2007/0049672 | A1 | 3/2007 | Norris |
| 2012/0052316 | A1 | 3/2012 | Evstatieva et al. |
| 2013/0217912 | A1 | 8/2013 | Garlichs et al. |

FOREIGN PATENT DOCUMENTS

| | | | |
|---|---|---|---|
| CN | 101475584 | | 7/2009 |
| CN | 102584652 | | 7/2012 |
| CN | 102796282 | | 11/2012 |
| EP | 0124833 | | 11/1984 |
| GB | 1572137 | | 7/1980 |
| JP | S55127358 | | 10/1980 |
| JP | H07258491 | | 10/1995 |
| JP | 08-143582 | * | 6/1996 |
| JP | 2008023523 | | 2/2008 |
| WO | WO2012025545 | | 3/2012 |
| WO | WO2018073362 | | 4/2018 |
| WO | 2020047129 | | 3/2020 |

OTHER PUBLICATIONS

Machine English translation of JP 08-143582, Hideo et al., Jun. 1996.*
European Search Report, for Application No. EP19854977.6, PCT/US2019/048612 (Apr. 13, 2022).
International Search Report and Written Opinion of the International Searching Authority for PCT/US2020/043440, Nov. 25, 2020.
International Search Report and Written Opinion of the International Searching Authority for PCT/US2019/048612, Jan. 3, 2020.
Notification of Reasons for Refusal from Japanese Patent Office, dated Aug. 1, 2023.
Office Action No. 16727 from Colombian Patent Office, dated Oct. 12, 2023.

* cited by examiner

*Primary Examiner* — Patrick D Niland
(74) *Attorney, Agent, or Firm* — Stone Pigman Walther Wittmann, L.L.C.; Mackenzie D. Rodriguez

(57) ABSTRACT

A novel Low Free 2-MercaptoEthanol Ester has been used to prepare Alkyl Tin Reverse Ester Stabilizers as well as used to enhance the thermal performance of those Alkyl Tin Reverse Ester Stabilizers or Alkyl Tin Thioglycolate Stabilizers or Alkyl Tin Mercaptides for PVC applications where odor during PVC compounding, processing, or of the final PVC article has prevented widespread use of Alkyl Tin Reverse Ester Stabilizers.

10 Claims, No Drawings

LOW FREE 2-MERCAPTOETHANOL ESTER AND USES THEREOF

CROSS-REFERENCE TO RELATED APPLICATIONS

This application is a continuation of U.S. patent application, Ser. No. 16/554,275, filed on 28 Aug. 2019, which claims the benefit of U.S. Provisional Patent Application, Ser. No. 62/723,943, filed on 28 Aug. 2018; and U.S. Provisional Patent Application, Ser. No. 62/878,040, filed on 24 Jul. 2019, both of which are hereby incorporated herein by reference. Priority of U.S. Provisional Patent Application, Ser. No. 62/723,943, filed on 28 Aug. 2018; and, U.S. Provisional Patent Application, Ser. No. 62/878,040, filed on 24 Jul. 2019, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to low free 2-mercaptoethanol esters and uses thereof. More particularly, the present invention relates to use of low free 2-mercaptoethanol esters to enhance thermal stabilizers for halogen-containing polymers, for example polyvinyl chloride or PVC.

2. General Background of the Invention

PVC is a thermally unstable polymer at traditional processing temperatures and many stabilizer systems have been developed that attempt to address its inherent thermal instability. These technologies include organic, mixed metal and tin-based stabilizers. Tin-based stabilizers broadly fall into two main technologies: Thioglycolic acid (TGA) or reverse ester (RE). TGA or 2-Ethyhexyl methacrylate (EHMA) based stabilizers have been used successfully since the 1950s while reverse ester, RE, stabilizers were introduced in the 1970s. The majority of tin-based PVC thermal stabilizers contain both monoalkyl and dialkyl components. This class of stabilizers has also been modified to contain sulfur bridging which can improve both performance and costs relative to their non-bridged counterparts. (see U.S. Pat. No. 3,565,931).

U.S. Pat. No. 4,062,881 by Kugele teaches that synergistic stabilizer performance occurs when a free mercaptan is added to a tin mercaptan. More recent developments from U.S. Pat. No. 6,846,861 by Herzig et. al teaches that organotin mercaptoalkyl heptonaotes provide improved fragrance over traditional mercapto esters such as 2-mercaptoethyl tallate, 2-mercaptoethyl oleate and others. However, this approach is hindered for regulatory and commercial reasons and this approach has not achieved commercial success. The use of 2-mercaptoethanol esters, hereafter referred to as 2ME esters, is generally accepted in PVC applications where odor has generally not found to be of concern such as PVC pipe, PVC siding substrate and PVC fencing substrate. There are other applications such as window profile and calendaring where odors created during downstream processing such as through blending, extrusion, calendaring, cutting, welding have been found to be unacceptable. Typical esters based on 2ME which are intended for production of tin-based stabilizers can contain up to 3 weight % residual or free 2ME. The residual 2ME in 2ME-based esters can be the result of excess 2ME used to increase yields of the desired 2ME esters. As well, the tin stabilizers produced therefrom can also contain up to 2 weight % residual 2-ME. Furthermore, additional 2ME may also be post-added to a reverse ester stabilizer to improve some aspects of the performance of the final 2ME-based ester stabilizer.

The following US Patents are incorporated herein by reference:

Kugele U.S. Pat. No. 4,062,881; and
Herzig et al. U.S. Pat. No. 6,846,861.

BRIEF SUMMARY OF THE INVENTION

The present invention is a stabilizer composition for halogen-containing polymer. It has recently been found that the odor of the 2ME Esters, and the resulting tin-based stabilizers derived therefrom, can be dramatically improved by significant reduction of the residual 2-Mercaptoethanol from the ester. This effect can be achieved in several manners to include but not limited to: washing with water, stripping out under heat and vacuum, using additional water to aid its removal under heat and vacuum, molecular sieves or membrane separation technologies.

It should also be noted that it is generally recognized that performance of tin-based stabilizers for halogen containing polymers is directly related to tin content of the tin stabilizer. However, 2ME ester-extended stabilizers provide surprising performance given that their thermal performance is in line with higher tin content stabilizers thus showing a higher thermal performance efficacy than what would be expected based solely on tin content.

2ME-based esters when used as boosters for tin-based stabilizers offer cost advantages over other approaches, such as Epoxidized Soybean Oil, commonly referred to as ESO. ESO has been used in both flexible and rigid PVC applications for many years as a co-stabilizer to boost performance of both Ca/Zn-based and tin-based stabilizer systems. ESO has typically been used due to its low odor coupled with low cost relative to tin-based stabilizers. The color development as outlined in Table 1 indicates that Low Free 2-Mercapto-Ethanol Ester (LFMEE) affords similar performance to ESO but the use of LFMEE also avoids shelf stability problems which are commonly seen with ESO-based tin stabilizers.

TABLE 1

PVC COMPOUND FORMULATION

| COMPONENT | PHR 1 | PHR 2 |
|---|---|---|
| PVC Resin (SE-750) or equivalent | 100.0 | 100.0 |
| Sample 1 | 2.00 | |
| Sample 2 | | 2.00 |
| Calcium Stearate | 1.2 | 1.2 |
| Paraffin 165 | 0.8 | 0.8 |
| E-14 Oxidized Polyethylene | 0.1 | 0.1 |
| K400 Acrylic Polymeric Modifier | 6.0 | 6.0 |

TABLE 1-continued

PVC COMPOUND FORMULATION

| | PHR | |
|---|---|---|
| COMPONENT | 1 | 2 |
| K175 Acrylic Polymeric Modifier | 1.0 | 1.0 |
| CaCO3-UFT Filler | 5.0 | 5.0 |
| TiO2 Pigment | 1.0 | 1.0 |

Test Conditions: The PVC compound was blended following standard additive addition order and temperature. The color stability of each compound was evaluated using a Brabender running operating at 190 degrees Celsius/60 rpm with samples taken in 2-minute intervals. The colors of each chip were measured relative to a standard white tile and "L Values" reported in the Table 2 below.

TABLE 2

Color Values

| Time | Color Value (L Value) | |
|---|---|---|
| (Min) | Sample 1 | Sample 2 |
| 2 | 90.75 | 91.01 |
| 4 | 88.98 | 90.37 |
| 6 | 88.1 | 89.58 |
| 8 | 86.41 | 87.790 |
| 10 | 86.25 | 88.25 |
| 14 | 85.49 | 86.07 |
| 18 | 80.03 | 79.04 |
| 22 | 65.78 | 66.15 |

Sample 1 85 Wt % ADVASTAB ® TM-181FS/15 WT % LFMEE
Sample 2 85 Wt % ADVASTAB ® TM-181FS/15 WT % Epoxidized Soybean Oil The samples above were prepared with ADVASTAB® brand TM-181FS; however, it is expected that similar results would be obtained with a generic compound of similar composition.

The present invention also provides the advantage of exploiting the renewable sourcing of fatty acids for the production of the 2-Mercaptoethyl Esters. In contrast, TGA or EHMA-based stabilizers are based entirely on oil-derived intermediates.

DETAILED DESCRIPTION OF THE INVENTION

All experiments to remove residual 2-Mercaptoethanol utilized standard 2-Mercaptoethyl Ester prepared in commercial equipment at PMC Organometallix. The process involves reacting 2-Mercaptoethanol with a C16-C18 fatty acid using an acid catalyst. As representative methods for preparation, the following three methods will be discussed in detail for the production of LFMEE:

Synthesis of Standard 2-Mercaptoethyl Ester:

In the following experiments, the 2-Mercaptoethyl Ester was prepared by reacting one equivalent of Fatty Acid to 1.18 moles of 2-Mercaptoethanol in the presence of an acid catalyst, heating slowly to 80-85 degrees Celsius under vacuum. The water of esterification is removed to drive the reaction. This reaction mixture is then water washed to remove the acid catalyst, the wash water split off, and then the organic layer dried under vacuum and heat.

Any other acceptable method of preparing standard 2-ME Ester may also be used.

Experiment A: 300 grams of Standard 2-Mercaptoethyl Ester was washed 10× with 100-gram aliquots of water. The washing occurred in a 500 ml separatory funnel and allowed to settle for 30 minutes. The water (bottom phase) was drained off and the next aliquot of water added. After the final wash was complete, the organic phase was dried by applying vacuum and heating to 110 C.

Experiment B: 100 grams of Standard 2-Mercaptoethyl Ester was treated 4×2.5 grams water. The Standard 2-Mercaptoethyl Ester was heated to 70 C then the 2.5-gram water aliquot was added. The water was removed by applying vacuum and heating to 70 C. Once temperature was achieved the next 2.5-gram aliquot of water was added. This was repeated for all 4 water aliquots.

Experiment C: 450 grams of Standard 2-Mercaptoethyl Ester was treated with 112 grams water, and the water was then removed under vacuum and heated to 85 C.

The % 2-Mercaptoethanol removed was determined by measuring the % Mercaptosulfur drop compared to the starting standard 2-Mercaptoethyl Ester.

TABLE 3

2ME removal from 2ME ester

| Exp. | Initial % Mercapto- sulfur | % Appox. 2-ME | Final % Mercapto- sulfur | % 2-ME Removed | % Approx. 2-ME | % Approx. 2-ME Removal |
|---|---|---|---|---|---|---|
| A | 9.12 | 2.8 | 8.18 | 2.22 | 0.6 | 80 |
| B | 9.09 | 2.8 | 8.02 | 2.52 | 0.3 | 90 |
| C | 9.09 | 2.8 | 7.94 | 2.70 | 0.1 | >95 |

Experiments A, B and C provided high levels of free 2-ME removal. The resulting lower free 2-ME esters were used in subsequent study to determine their efficacy as co-stabilizers and/or as incorporated as a bound species within a tin-based stabilizer but without the traditional offensive odors resulting from the use of higher free 2-ME esters. Other acceptable methods of removing 2-ME from 2-ME Esters to produce the novel LFMEE of the present invention may also be used.

Description of Stabilizer Preparation

ADVASTAB® TM-181FS was prepared using the following process:

1.03 equivalent (eq) of 2-Ethylhexyl Thioglycolate, was reacted with an aqueous mixture of Monomethyl Tin Trichloride (25 wt %) and Dimethyl Tin Dichloride (75 wt %) representing 1.0 equivalents of chloride using aqueous Sodium Hydroxide aqueous solution to convert the Chloride to the Mercaptide. This mixture is allowed to settle for 60 minutes for the organic and aqueous phases to split. The bottom organic layer is removed dried under vacuum and heat. This layer was then filtered to yield a clear liquid.

TABLE 4

ADVASTAB ® TM-181FS* is blended with the specified % LFMEE as indicated below

| SAMPLE # | ADVASTAB ® TM-181FS | LFMEE % | PHR | PHR Tin |
|---|---|---|---|---|
| 1 | 100% | 0% | 2.0 | 0.38 |
| 2 | 95% | 5% | 2.0 | 0.361 |
| 3 | 90% | 10% | 2.0 | 0.342 |
| 4 | 85% | 15% | 2.0 | 0.323 |
| 5 | 80% | 20% | 2.0 | 0.304 |
| 6 | 75% | 25% | 2.0 | 0.285 |

TABLE 5

These samples were compounded into PVC formulation as shown

| Component | PHR 1 | 2 | 3 | 4 | 5 | 6 |
|---|---|---|---|---|---|---|
| PVC (SE-750) or equivalent | 100.0 | 100.0 | 100.0 | 100.0 | 100.0 | 100.0 |
| Sample 1 | 2.00 | | | | | |
| Sample 2 | | 2.00 | | | | |
| Sample 3 | | | 2.00 | | | |
| Sample 4 | | | | 2.00 | | |
| Sample 5 | | | | | 2.00 | |
| Sample 6 | | | | | | 2.00 |
| Calcium Stearate | 1.2 | 1.2 | 1.2 | 1.2 | 1.2 | 1.2 |
| CS-2054 Lubricant | 0.8 | 0.8 | 0.8 | 0.8 | 0.8 | 0.8 |
| E-14 Lubricant | 0.1 | 0.1 | 0.1 | 0.1 | 0.1 | 0.1 |
| K400 Acrylic Modifier | 6.0 | 6.0 | 6.0 | 6.0 | 6.0 | 6.0 |
| K175 Acrylic Modifier | 1.0 | 1.0 | 1.0 | 1.0 | 1.0 | 1.0 |
| CaCO3 - UFT Filler | 5.0 | 5.0 | 5.0 | 5.0 | 5.0 | 5.0 |
| TiO2 Pigment | 1.0 | 1.0 | 1.0 | 1.0 | 1.0 | 1.0 |

TABLE 6

Color Values for TM181FS and LFMEE blends

Color Values (L Value)

| Time (Min) | Sample 1 | Sample 2 | Sample 3 | Sample 4 | Sample 5 | Sample 6 |
|---|---|---|---|---|---|---|
| 2 | 90.77 | 92.39 | 93.91 | 91.80 | 93.01 | 92.79 |
| 4 | 90.84 | 92.1 | 93.07 | 90.66 | 92.46 | 93.05 |
| 6 | 91.2 | 91.85 | 93.33 | 89.74 | 91.71 | 92.43 |
| 8 | 91.48 | 92.77 | 94.04 | 90.23 | 92.12 | 93.4 |
| 10 | 91.78 | 93.06 | 94.3 | 90.15 | 93.35 | 93.64 |
| 14 | 92.9 | 91.94 | 92.7 | 94.49 | 93.27 | 93.02 |

* ADVASTAB® TM-181FS was provided by PMC Organometallix, Inc. It is an industry standard for numerous PVC applications. Other suitable stabilizers may be used. Preferred stabilizer compositions may include compositions similar to the general composition of ADVASTAB® TM-181FS shown below:

| Alkyl Group Type | Ligand Type | Wt % Mono | Wt % Tin |
|---|---|---|---|
| Methyl | 2-EHMA | 27 | 19.0 |

PVC blends using stabilizer compositions in Table 5 were subjected to 2 roll mill performance testing and the corresponding color data (L values) are outlined in Table 6. As indicated in Table 6, blends of tin stabilizer with up to 25 weight % of LFMEE provided similar performance to the control stabilizer. It should be further noted that the performance of, for examples, Samples 5 and 6 is achieved with significantly lower tin contents.

Procedure for Synthesis of Stabilizer A and B:

During the preparation of the PVC blends for the evaluations, it was observed that the odor of the blend of ADVASTAB® TM-181FS and LFMEE had an odor similar to that of the unmodified ADVASTAB® TM-181FS. The odor of the ADVASTAB® TM-181FS with standard 2-Mercaptoethyl Ester, i.e. an ester with >2% by weight free 2-ME, had a noticeably stronger, unpleasant odor. It is expected that similar outcomes would be achieved with a similar composition generic stabilizer.

The utility of LFMEEs in the synthesis of stabilizers was also investigated. The performance of high monooctyltin stabilizers based on LFMEE was compared to its 2-EHMA analogue, commercially available Thermolite 895. In the context of this work high monooctyltin refers to tin-based stabilizers with a mono content greater than 75% with the corresponding di content less than 25% and the examples below are based on materials with a mono content greater than 90%. The high monooctyl tin-based LFMEE was prepared from high monooctyl chloride in a conventional manner as detailed in the Experimental section. Tin content was directed toward a high monooctyltin LFMEE stabilizer which contains a tin content to allow comparison of stabilizers within a narrower range of tin weight percentages which allows different stabilizers to be compared at equal tin contents and therefore similar loading levels. This approach reduces or removes any effects on performance from different loading levels of the thermal stabilizer. Thus, a sulfided version of the original high monooctyltin LFMEE was produced by methodology familiar to one skilled in the art of stabilizer production through the use of high monooctyl tin chloride, LFMEE and sodium sulfide (see examples for details). This material is described as high monooctyl LFMEE sulfide and will be referred to as Stabilizer A. Initially, these stabilizers were compared on an equal tin basis and evaluated on a 2-roll mill stability test. These results are summarized in Table 8.

Description of Stabilizer Preparation

THERMOLITER 895 and Stabilizer A were prepared using the following process:

1.02 eq of Mercapto Sulfur containing ester (for THERMOLITER 895 this is 2-Ethylhexyl Thioglycolate, for Stabilizer A this is a combination of LFMEE and Disodium Sulfide) were reacted with a mixture of Monooctyl Tin Trichloride (95 wt %) and Dioctyl Tin Dichloride (5 wt %) representing 1.0 equivalents of chloride using aqueous Sodium Hydroxide aqueous solution to convert the Chloride to the Mercaptide. This mixture is allowed to settle for 60 minutes to allow the organic and aqueous phases to split. The bottom aqueous layer is removed and the remaining organic phase was dried under vacuum and heat. This was then filtered to yield a clear liquid. Generic equivalents of THERMOLITER 895 can be used. It is expected that similar outcomes will occur with a generic equivalent of THERMOLITE® 895.

These stabilizers were evaluated for their effect on PVC processing, in particular their impact of color developing as function of heat and time. These stabilizers were compounded in the PVC formulation shown in Table 7.

TABLE 7

PVC Formulations of Stabilizers

| Component | PHR Sample1 | Sample 2 |
|---|---|---|
| Shintech® SE-750 PVC resin | 100.0 | 100.0 |
| THERMOLITE ® 895 | 1.15 | |
| Stabilizer A | | 1.16 |
| Calcium Stearate | 0.2 | 0.2 |
| CS-2054 Lubricant | 0.7 | 0.7 |
| Arkema ® P-530 (Polymeric Modifier) | 1.0 | 1.0 |
| Arkema ® P-770 (Polymeric Modifier) | 1.0 | 1.0 |
| Arkema ® C-859 (Polymeric Modifier) | 8.0 | 8.0 |
| Omya ® UFT CaCO3 Filler | 5.0 | 5.0 |
| Chemours ® 960 TiO2 Pigment | 0.5 | 0.5 |

Generic equivalents of name brand components can be used. It is expected that similar outcomes will occur with use of generic equivalents of name brand components.

TABLE 8

Stabilizers Stability Test

| Time (Min) | Color Values (L Value) | |
|---|---|---|
| | Sample 1 | Sample 2 |
| 2 | 90.30 | 91.94 |
| 4 | 90.63 | 91.56 |
| 6 | 88.70 | 92.11 |
| 8 | 88.28 | 92.95 |
| 10 | 84.03 | 93.09 |
| 12 | | 87.86 |

| SAMPLE | DESCRIPTION | PHR | % TIN | PHR Tin |
|---|---|---|---|---|
| 1 | THERMOLITE ® 895 | 1.15 | 13.6 | |
| 2 | Stabilizer A | 1.16 | 13.5 | |

As shown by the L values in Table 8, it can be clearly seen that Stabilizer A provides better early color, better color development and term stability versus the control, T895, which is a traditional EHMA-based stabilizer.

To better understand if the improved performance of the LFMEE-based stabilizers can be extended to lower mono stabilizers, a LFMEE-based stabilizer was prepared from a 25% mono/75% di starting material in order to compare to the commercially available, T890F, which has a similar mono/di ratio. T895 and T890F are both used for a variety of rigid PVC applications but find use particularly in film and sheet applications. The performance of these materials was compared at equal tin content on a 2-roll mill to evaluate color development, term stability and relative odor and roll stickiness and the results are summarized in Table 10 and Table 11.

These stabilizers were evaluated for their effect on PVC processing, in particular their impact of color developing as function of heat and time. These stabilizers were compounded in the PVC formulation shown in Table 9.

TABLE 9

Stabilizer Compositions

| | PHR | |
|---|---|---|
| COMPONENT | Sample 1 | Sample 2 |
| Shintech ® SE-750 PVC resin | 100.0 | 100.0 |
| THERMOLITE ® 890F | 1.00 | |
| Stabilizer B | | 1.05 |
| Calcium Stearate | 0.2 | 0.2 |
| CS-2054 Lubricant | 0.7 | 0.7 |
| Arkema ® P-530 (Polymeric Modifier) | 1.0 | 1.0 |
| Arkema ® P-770 (Polymeric Modifier) | 1.0 | 1.0 |
| Arkema ® C-859 (Polymeric Modifier) | 8.0 | 8.0 |
| Omya ® UFT CaCO3 | 5.0 | 5.0 |
| Chemours ® 960 TiO2 | 0.5 | 0.5 |

Generic equivalents of name brand components can be used. It is expected that similar outcomes will occur with use of generic equivalents of name brand components.

TABLE 10

L Value Data

| Time | Color Values (L Value) | |
|---|---|---|
| (Min) | Sample 1 | Sample 2 |
| 2 | 89.03 | 88.30 |
| 4 | 88.36 | 88.62 |
| 6 | 86.89 | 87.04 |
| 8 | 84.45 | 86.21 |
| 10 | 74.42 | 83.22 |

| SAMPLE | DESCRIPTION | PHR | % TIN | Phr Tin |
|---|---|---|---|---|
| 1 | THERMOLITE ® 890F | 1.0 | | |
| 2 | Stabilizer B | 1.05 | | |

Generic equivalents of name brand components can be used. It is expected that similar outcomes will occur with use of generic equivalents of name brand components.

As can be seen in Table 10, the performance of Stabilizer B outperforms that of Thermolite® 890F in terms of color development which indicates that the improved performance of LFMEE-based stabilizers can be found across a wide range of mono/di.

TABLE 11

Relative Subjective Odor and Roll Stickiness During Processing

| | T890F | T895 | Stabilizer A |
|---|---|---|---|
| Odor | Unpleasant | Unpleasant | Less unpleasant |
| Stickiness | High | High | Low |

Generic equivalents of name brand components can be used. It is expected that similar outcomes will occur with use of generic equivalents of name brand components.

At similar loading levels, Stabilizer A provided improved color stability and term stability relative to T890F and T895. Additionally, it provided improved roll stickiness and odor during processing. These performance characteristics are critically important for film produced by calendaring which is a process that requires release of the hot plastic melt from hot processing rolls to produce a sheet or film. A large hot, surface area is created during the calendaring process so an improvement in odor can also provide benefit for the production environment.

Further work was directed at exploring the relative efficiency of Stabilizer A versus its EHMA-based counterpart, T895. Samples were prepared for study with a 2 roll mill in stability test uses the PVC formulation described used to produce data in Table 8 above. The results the results are summarized in Table 12.

TABLE 12

Color values (L value) T895 and Stabilizer A at reduced loading

| Time | Color Values (L Value) | | | |
|---|---|---|---|---|
| (Min) | Sample 1 | Sample 2 | Sample 3 | Sample 4 |
| 2 | 90.07 | 89.72 | 91.87 | 89.69 |
| 4 | 91.21 | 89.26 | 92.03 | 89.18 |
| 6 | 90.54 | 88.67 | 92.35 | 89.41 |
| 8 | 90.48 | 90.60 | 92.93 | 90.55 |

TABLE 12-continued

Color values (L value) T895 and Stabilizer A at reduced loading

| Time | Color Values (L Value) | | | |
|---|---|---|---|---|
| (Min) | Sample 1 | Sample 2 | Sample 3 | Sample 4 |
| 10 | 83.53 | 90.40 | 91.73 | 90.09 |
| 12 | | 86.12 | | |

TABLE 13

Sample Descriptions

| SAMPLE | DESCRIPTION | PHR |
|---|---|---|
| 1 | THERMOLITE ® 895 | 1.15 |
| 2 | STABILIZER A | 1.16 |
| 3 | STABILIZER A | 1.08 |
| 4 | STABILIZER A | 1.00 |

Generic equivalents of name brand components can be used. It is expected that similar outcomes will occur with use of generic equivalents of name brand components.

Table 12 indicates that at lower loading levels Stabilizer A provides better color development that T895 with similar term stability. All else being equal, one can conclude that Stabilizer A will provide a more cost-effective stabilizer solution than its EHMA-based analogue along with improved processing.

The offensive odor of the 2-Mercaptoethanol can also be addressed by having it react as a ligand with an Alkyl Tin Halide intermediate. This conversion of 2-Mercaptoethanol to a tin-bound mercaptoethanol ligand would reduce volatility and improve odor characteristics. This potential route, however, suffers from the need for precise control of stoichiometry which, if not controlled, can lead to undesired side products.

A further alternate means of reacting not only the residual 2-Mercaptoethanol but also any other active mercaptan group is the use of adding an Alkyl tin Oxide which is capable to scavenging the mercaptan through reacting with the mercaptan to form an Alkyl Tin Mercaptide. Examples of the alkyl tin oxide include, but are not limited to, Dioctyl Tin Oxide, Dibutyl Tin Oxide, Butyl Stannoic Acid, and Octyl Stannoic Acid.

In the present invention, a Low Free 2-MercaptoEthanol Ester (LFMEE) that is obtained through removal of 2-MercaptoethylEthanol from a standard 2-MercaptoEthanol Ester, wherein the resulting LFMEE have residual 2-Mercaptoethanol below 1.0 wt %.

In certain embodiments, the resulting LFMEE can have residual 2-Mercaptoethanol below 0.7 wt %.

In certain embodiments, the resulting LFMEE have residual 2-Mercaptoethanol below 0.5 wt %.

The present invention presents a method of using the aforementioned LFMEE to enhance thermal performance of alkyl tin thioglycolate ester stabilizers.

The present invention presents a method of using the aforementioned LFMEE to enhance thermal performance of alkyl tin reverse ester stabilizers.

The present invention presents a method of using the aforementioned LFMEE to enhance thermal performance of alkyl tin mercaptide stabilizers.

In certain embodiments, the mercaptide can be dodecylmercaptan or carboxylates.

In certain embodiments, the mercaptide can be Maleates.

In certain embodiments of the present invention, the stabilizer further includes sulfide bridging for alkyl groups ranging of C1-C8.

In certain embodiments of the present invention, the mono and di components of alkyl tin groups are in ratios ranging from 100% di to 100% mono and all combinations between.

In certain embodiments of the present invention, the amount of LFMEE can range from 5 wt % to 75 wt %.

In certain embodiments of the present invention, the amount of LFMEE can range from 10 wt % to 40 wt %.

In certain embodiments of the present invention, the resulting stabilizer further includes Ca/Zn-based boosters, organic-based stabilizers and/or other traditional performance boosters such as BHT, polyols, metallic salts or other co-stabilizers.

The present invention can include a composition comprising:
  (a) an alkyl tin reverse ester stabilizer:and
  (b) a LFMEE of claims 1-3:
wherein the ratio of alkyl tin reverse ester stabilizer:LFMEE ranges from 95 wt %:5 wt % to 25 wt %: 75 wt %.

In the present invention, the composition can include a ratio of alkyl tin reverse ester stabilizer:LFMEE ranges from 85 wt %:15 wt % to 60 wt %:40 wt %.

The present invention can comprise a method of using the LFMEE that is obtained through removal of 2-MercaptoethylEthanol from a standard 2-MercaptoEthanol Ester, wherein the resulting LFMEE have residual 2-Mercaptoethanol below 1.0 wt %, as a ligand with 2-EHMA, carboxylates, lauryl mercaptan, 2-Mercaptoethanol, thioglycolic acid, alkoxides or sulfide.

The present invention can comprise a method wherein the aforementioned LFMEE is used along with other ligands in combinations with 2-EHMA, carboxylates, lauryl mercaptan, 2-Mercaptoethanol, thioglycolic acid, alkoxides or sulfide.

The present invention can comprise a method of preparing a PVC stabilizer, the method comprising:
  (a) reacting 1.02 eq of the LFMEE that is obtained through removal of 2-MercaptoethylEthanol from a standard 2-MercaptoEthanol Ester, wherein the resulting LFMEE have residual 2-Mercaptoethanol below 1.0 wt %, and Disodium Sulfide, with a mixture of Monooctyl Tin Trichloride (95 wt %) and Dioctyl Tin Dichloride (5 wt %) representing 1.0 equivalents of chloride using aqueous Sodium Hydroxide aqueous solution:
  (b) allowing the mixture to settle:
  (c) removing the bottom aqueous layer:
  (d) drying the remaining organic phase:and
  (e) filtering the dried organic phase.

The present invention can comprise the aforementioned method wherein the drying step (d) is done under vacuum.

The present invention can comprise the aforementioned method wherein the drying step (d) is done under heat.

The present invention can comprise the aforementioned method wherein the drying step (d) is done under vacuum and heat.

The present invention can comprise the aforementioned method wherein step (e) is carried out until it yields a clear liquid.

Acronym List

2ME 2-mercaptoethanol
EHMA 2-Ethyhexyl methacrylate
ESO Epoxidized Soybean Oil
LFMEE Low Free 2-MercaptoEthanol Ester PHR parts per hundred resin
PVC polyvinyl chloride
RE reverse Ester
RPM revolutions per minute
TGA thioglycolic acid

The invention claimed is:

1. A method of using a Low Free 2-MercaptoEthanol Ester (LFMEE) that is obtained through removal of 2-MercaptoEthanol from a standard 2-MercaptoEthanol Ester, wherein the resulting LFMEE have residual 2-Mercaptoethanol below 1.0 wt % to enhance thermal performance of alkyl tin thioglycolate ester stabilizers, wherein the standard 2-MercaptoEthanol Ester is formed by a reaction of 2-mercaptoethanol with C16-C18 fatty acid, the method comprising:
   blending LFMEE with the alkyl tin thioglycolate ester stabilizer,
   wherein the LFMEE and stabilizer are combined in a ratio ranging from 5 wt % LFMEE:95 wt % stabilizer to 25 wt % LFMEE:75 wt % stabilizer.

2. A method of using a Low Free 2-MercaptoEthanol Ester (LFMEE) that is obtained through removal of 2-MercaptoEthanol from a standard 2-MercaptoEthanol Ester, wherein the resulting LFMEE have residual 2-Mercaptoethanol below 1.0 wt % to enhance thermal performance of alkyl tin reverse ester stabilizers, wherein the standard 2-MercaptoEthanol Ester is formed by a reaction of 2-mercaptoethanol with C16-C18 fatty acid, the method comprising steps of:
   blending LFMEE with the alkyl tin reverse ester stabilizer,
   wherein the LFMEE and stabilizer are combined in a ratio ranging from 5 wt % LFMEE:95 wt % stabilizer to 25 wt % LFMEE:75 wt % stabilizer.

3. A method of using a Low Free 2-MercaptoEthanol Ester (LFMEE) that is obtained through removal of 2-MercaptoEthanol from a standard 2-MercaptoEthanol Ester, wherein the resulting LFMEE have residual 2-Mercaptoethanol below 1.0 wt % to enhance thermal performance of alkyl tin mercaptide and carboxylate stabilizers, wherein the standard 2-MercaptoEthanol Ester is formed by a reaction of 2-mercaptoethanol with C16-C18 fatty acid, the method comprising steps of:
   combining LFMEE with the alkyl tin mercaptide and carboxylate stabilizer,
   wherein the LFMEE and stabilizer are combined in a ratio ranging from 5 wt % LFMEE:95 wt % stabilizer to 25 wt % LFMEE: 75 wt % stabilizer.

4. The method of claim 3 wherein the mercaptide is chosen from the group consisting of dodecylmercaptan or carboxylates.

5. The method of claim 3 wherein the carboxylate is Maleates.

6. The method of claim 3 wherein the stabilizer further includes sulfide bridging for alkyl groups ranging of C1-C8.

7. The method of claim 3 wherein the alkyl tin stabilizers comprise alkyl tin groups, and the alkyl tin groups can include monooctyl tin and dioctyl tin components, wherein the monooctyl tin and dioctyl tin components of the alkyl tin groups are in ranges from 0 wt % to 100 wt % dioctyl tin and 0 wt % to 100 wt % monooctyl tin and all combinations between.

8. The method of claim 1 wherein the resulting stabilizer composition further comprises a booster, the booster chosen from the group consisting of: Ca/Zn-based boosters, organic-based stabilizers, BHT, polyols, metallic salts or other co-stabilizers.

9. The method of claim 1 wherein the LFMEE and stabilizer are combined in a ratio ranging from 0 wt % LFMEE:90 wt % stabilizer to 15 wt % LFMEE:85 wt % stabilizer.

10. The method of claim 3 wherein the LFMEE and stabilizer are combined in a ratio ranging from 0 wt % LFMEE:90 wt % stabilizer to 15 wt % LFMEE:85 wt % stabilizer.

* * * * *